(12) United States Patent
Belkind et al.

(10) Patent No.: US 8,273,389 B2
(45) Date of Patent: Sep. 25, 2012

(54) COMPOSITIONS COMPRISING CINNAMON OIL (AND/OR ITS COMPONENT CINNAMALDEHYDE) AND DIALLYL DISULFIDE, THEIR FORMULATIONS, AND METHODS OF USE

(75) Inventors: Benjamin A. Belkind, Wilmette, IL (US); Bassam Shammo, Mundelein, IL (US); Rebecca Dickenson, Volo, IL (US); Linda A. Rehberger, Glenview, IL (US); Daniel F. Heiman, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 284 days.

(21) Appl. No.: 12/580,391

(22) Filed: Oct. 16, 2009

(65) Prior Publication Data

US 2010/0098787 A1    Apr. 22, 2010

Related U.S. Application Data

(60) Provisional application No. 61/106,186, filed on Oct. 17, 2008.

(51) Int. Cl.
*A61K 36/54* (2006.01)
*A61K 36/8962* (2006.01)

(52) U.S. Cl. .................................. 424/739; 424/754

(58) Field of Classification Search .................. None
See application file for complete search history.

(56) References Cited

U.S. PATENT DOCUMENTS

| 4,080,191 A * | 3/1978 | Harvey ..................... 504/155 |
| 5,051,255 A | 9/1991 | Devidas et al. |
| 5,057,141 A | 10/1991 | Rodriquez-Kabana et al. |
| 5,182,207 A | 1/1993 | Ward et al. |
| 5,360,607 A | 11/1994 | Eyal et al. |
| 5,439,934 A | 8/1995 | Wood et al. |
| 6,231,865 B1 | 5/2001 | Hsu et al. |
| 6,251,951 B1 | 6/2001 | Emerson et al. |
| 6,750,256 B1 | 6/2004 | Crandall, Jr. et al. |
| 7,019,036 B2 | 3/2006 | Hiromoto et al. |
| 2003/0005484 A1 | 1/2003 | Crandall, Jr. et al. |
| 2004/0235668 A1 | 11/2004 | Abribat et al. |
| 2005/0038094 A1 * | 2/2005 | Warrington ................. 514/383 |
| 2007/0042182 A1 * | 2/2007 | Markus et al. ............. 428/402.2 |

FOREIGN PATENT DOCUMENTS

| DE | 3638290 A * | 5/1988 |
| EP | 379851 A1 * | 8/1990 |
| EP | 945066 A1 * | 9/1999 |

OTHER PUBLICATIONS

Y.Oka, "Nematicidal activity of essential oil components against the root-knot nematode Meloidogyne javanica", Nematology, 2001, vol. 3(2), pp. 159-164.
R. Pandy et al., "Essential oils as potent sources of nematicidal compounds", J. Phytopathology 148, 2000, pp. 501-502.
Block, "The organosulfur chemistry of the genus allium—implications for the organic chemistry of sulfur", Angew. Chem. Int. Ed. Engl. 1992, 31, pp. 1135-1178.

* cited by examiner

Primary Examiner — Christopher R. Tate
Assistant Examiner — Deborah A. Davis
(74) Attorney, Agent, or Firm — Wood, Phillips, Katz, Clark & Mortimer

(57) ABSTRACT

The invention relates to diallyl disulfide and cinnamon oil formulations, for protecting plants from nematodes and other plant pathogens. The invention provides a method for suppressing plant damage by nematodes and other plant pathogens, which comprises the concurrent administration, to the locus, soil or seeds of plants in need of such treatment, of (a) cinnamon oil (and/or its component cinnamaldehyde), (b) an effective quantity of diallyl disulfide, as well as nematocidal compositions useful therein.

16 Claims, No Drawings

COMPOSITIONS COMPRISING CINNAMON OIL (AND/OR ITS COMPONENT CINNAMALDEHYDE) AND DIALLYL DISULFIDE, THEIR FORMULATIONS, AND METHODS OF USE

FIELD OF THE INVENTION

The present invention relates to compositions useful in the control of agricultural pests such as nematodes or other plant pathogenic organisms. More particularly, the invention relates to synergistic combinations of a biopesticide obtained from Cinnamon oil (and/or its component cinnamaldehyde), and diallyl disulfide, in which the diallyl disulfide is applied at rates that are nematicidally ineffective if and when applied alone. The invention also relates to a method for suppressing plant damage by nematodes or other plant pathogenic organisms which comprises the concurrent administration, to the locus, soil or seeds of plants in need of such treatment, of (a) an effective amount of cinnamon oil (and/or its major component cinnamaldehyde), and (b) an effective quantity of diallyl disulfide, as well as nematocidal compositions useful therein.

BACKGROUND OF THE INVENTION

Plant parasitic nematodes cause serious economic damage to many agricultural crops around the world. The nematodes in this group are microscopic worms and are, in general, obligate parasites of plants. They feed mostly on the roots of host plants; however, several genera are known to parasitize above-ground parts including stems, leaves and flowers as well. Almost all the plant species of economic importance are susceptible to infection by some species of nematodes (notable exceptions are in the marigolds and asparagus). For example, root knot nematodes (RKN), (*Meloidogyne* spp.) are capable of parasitizing more than 3,000 species of crop plants. These plants include agronomic crops, vegetables, fruits, flowering trees and shrubs. Nematodes reportedly cause crop loss of more than six billion dollars in the United States alone and more than one hundred billion dollars around the world.

The symptoms due to parasitic nematode injury vary widely depending on the plant host, the nematode species, age of the plant, geographical location and climatic and external environmental conditions. In general, an overall patchy appearance of plants in a field is considered indicative of nematode infestation. More specifically, nematode injury results in galling of the roots (abnormal swelling in the tissue due to rapid multiplication of cells in the cortical region) caused by species of root knot (*Meloidogyne* spp.) and cyst (*Heterodera* spp.) nematodes, lesions (localized, discolored areas) caused by lesion nematodes (*Pratylenchus* spp.), suppression of cell division resulting in stubby roots (*Trichodorus* spp.), growth abnormalities including crinkling or twisting of above-ground parts (*Aphelenchoides* spp.), and even cell necrosis (death) in some cases. Plant parasitic nematodes may be endoparasitic in nature, as in the case of the root-knot and lesion nematodes, or ectoparasitic as in the dagger nematode (*Xiphinema* spp.) and lance nematode (*Hoplolaimus* spp.). Nematodes can be vectors of plant viruses and are also known to induce disease complexes predisposing plants to infection by other plant pathogenic fungi and bacteria.

Chemical nematocides, either soil fumigants or non-fumigants, have been in use for many years and are among the few feasible options for countering nematodes. At present, repeated applications of synthetic chemicals to the ground are required prior to planting the crop. These chemicals are extremely toxic to organisms besides nematodes and many of them may pose serious threats to the environment. With the renewed emphasis on clean water and air by environmental groups and governmental agencies, and the detection of many of these active ingredients or the metabolites thereof in ground water and several non-target organisms, there has been serious concern as to the manufacture and/or use of these chemicals. One of the most effective, economical, and widely used nematocides, DBCP (1,2-dibromo-3-chloropropane), found in ground water has been judged to induce male sterility and possible carcinogenesis. Another widely used chemical, EDB (ethylene dibromide), has also been found in ground water.

Yet another very common insecticide-nematocide, aldicarb (2-methyl-2-(methylthio)-propionaldehyde-O-(methylcarbamoyl)oxime), has been found to be acutely toxic. Aldicarb has been found in ground water in several regions of United States. Carbofuran (2,3-dihydro-2,2-dimethyl-7-benzofuranyl methylcarbamate) and 1,3-D (1,3-dichlorpropane), two very commonly used nematocides, are under special review by the EPA because of their avian toxicity and possible carcinogenic effects. More recently, the decision by the EPA to limit and eventually discontinue the use of the soil fumigant, methyl bromide, for agricultural purposes presents a threat to the efficiency and quality of agricultural production in the United States.

Natural isolates such as N-acetyl-D-glucosamine, which may be derived from microorganisms which are the waste products of industrial fermentation processes, have been disclosed as nematocidal in U.S. Pat. No. 5,057,141.

Biopesticides have been developed as an alternative to chemical pesticides. They are obtained by fermentation and can be used either as crude biomass or purified. Typically, fermentations are carried out at temperatures in the range of 20-40° C. For example, submerged fermentation at 28-30° C. of *Paecilomyces fumosoroues* fungal isolate ATCC No. 20874 produces fungal biomass for control of nematode infestation as disclosed in U.S. Pat. No. 5,360,607; whole fermentation broth from fermentation at 28° C. of *Streptomyces thermoarchaensis* NCIB 12015 is disclosed as nematocidal in U.S. Pat. No. 5,182,207; fermentation broth obtained from fermentation of *Streptomyces cyaneogriseus noncyanogenus* NRRL 15773 at 28° C. is effective against nematodes as disclosed in U.S. Pat. No. 5,439,934; and fermentation broth obtained by fermentation of the fungus *Myrothecium verrucaria* at temperatures of from 25 to 30° C. is disclosed as nematocidal in U.S. Pat. No. 5,051,255.

However, there is still a need for the development of new and effective nematocides. Plants were suggested as a source of effective pesticidal compounds as many plant essential oils exhibit antimicrobial, insecticidal, fungicidal, and herbicidal activity. They have been applied as pesticides for pest, disease and weed management.

Plant essential oils which do not present any known risk to humans or to the environment are qualified for an exemption as minimum risk pesticides and are listed in the 40 C.F.R. §152.25 (b). However, high volatility, phytotoxicity and low water solubility of some oils have limited their use in crop protection.

One plant essential oil used in agricultural applications is ProGuard® 30% Cinnamaldehyde Flowable Insecticide, Miticide, and Fungicide. See U.S. Pat. Nos. 6,750,256 B1 and 6,251,951 B1. However, a downside of this commercial product is that it contains the chemical preservative o-Phenylphenol.

Nematicidal activity of plant essential oils were reported, among others, by Y. Oka (Nematology, Vol. 3(2), pp. 159-164, 2001) and R. Pandey (J. Phytopathology 148, 501-502 (2000)). Essential oils of some plants and their components have been tested for nematicidal activity in vitro and in soil. Some plant essential oils which were determined to have nematicidal activity include essential oils of applemint (*Mentha rotundifolia*), caraway (*Carum carvi*), fennel (*Foeniculum vulgare*), oregano (*Origanum vulgare*), Syrian oregano (*Origanum syriacum*), and wild thyme (*Coridothymus capitatus*). Also, it was reported that aromatic and aliphatic aldehydes, including cinnamic aldehyde (also known as cinnamaldehyde) possess strong nematicidal activity in vitro. For example, U.S. Pat. No. 6,251,951 B1 demonstrates that cinnamaldehyde has nematicidal activity in the presence of 2% Tween 80 and 6% $NaHCO_3$ vehicle.

Accordingly, there is a need to develop more potent, yet safe and easy-to-use formulations to improve the biological effectiveness of nematicidal plant essential oils for agricultural applications.

SUMMARY OF THE INVENTION

It has now been found that by combining cinnamon oil (and/or its component cinnamaldehyde), with diallyl disulfide, effective suppression of nematodes is possible at biocontrol agent levels far below those needed when the individual nematode control agents are applied alone. Surprisingly, the combined effect is synergistic rather than merely additive, in that nematode control is possible by using application rates below those normally required for activity of both the metabolite and the synergistic chemical.

Accordingly, in one aspect of the present invention, a method is disclosed for the suppression of plant damage by nematodes which method comprises the concurrent administration, to the locus, soil or seeds of plants in need of such treatment, of (a) cinnamon oil (and/or its component cinnamaldehyde), and (b) diallyl disulfide. These two agents may be regarded as having been administered "concurrently" when applied either simultaneously, as in the form of a composition in which the agents are combined in the same preparation, or separately, but to the same plants, or soil, or seeds, in a manner such that both are present and active at the same time.

In one embodiment, the invention provides a formulation suitable for agricultural use comprising cinnamon oil, diallyl disulfide, at least one solvent selected from the group consisting of soybean oil, methyl oleate, ethyl lactate, and methyl soyate, and an emulsifier, wherein said formulation does not include an organic solvent, a surfactant, or a detergent. In a preferred embodiment, the emulsifier is polyethylene sorbitol hexaoleate.

In a preferred embodiment, cinnamon oil comprises from 10 to 50% by weight of the total formulation, diallyl disulfide comprises from 3 to 15% of the formulation, soybean oil comprises from 30 to 70% by weight of the total formulation, methyl oleate comprises about 10 to 25% by weight of the total formulation, and polyethylene sorbitol hexaoleate comprises about 5 to 15% by weight of the total formulation. The weight/weight ratio of cinnamon oil to the diallyl disulfide varies from about 3:1 to about 10:1.

In a more preferred embodiment, cinnamon oil comprises about 43% by weight of the total formulation, diallyl disulfide comprises about 7% of the formulation, soybean oil comprises about 30% by weight of the total formulation, methyl oleate comprises about 10% by weight of the total formulation, and polyethylene sorbitol hexaoleate comprises about 10% by weight of the total formulation.

In yet another embodiment, the invention provides a formulation suitable for agricultural use comprising cinnamon oil, diallyl disulfide, soybean oil, ethyl lactate and polyethylene sorbitol hexaoleate, wherein said formulation does not include an organic solvent, a surfactant, or a detergent. In a preferred embodiment, the total weight % of the cinnamon oil plus the diallyl disulfide comprises about 50% by weight of the total formulation.

In another embodiment, the invention provides a method of protecting a plant from at least one pathogen comprising applying to the plant an effective amount of the claimed formulations. In one embodiment, the pathogen may be a nematode.

In use the cinnamon oil is applied to a plant in an amount in the range of from 1 ppm to 5000 ppm, preferably 1 ppm to 1000 ppm and the diallyl sulfide is applied to a plant in an amount in the range of from 0.01 to 1000, preferably 1 to 100 ppm.

In one embodiment, the plant may be a cucumber; in another embodiment, the plant may be a melon; in yet another embodiment, the plant may be a tomato.

In one embodiment, the application of the formulation is performed by spraying.

In one embodiment, the effective amount is sufficient to provide an acceptable level of gall reduction.

In another embodiment, the effective amount is sufficient to inhibit growth of *Pythium*.

In yet another embodiment, the effective amount is sufficient inhibit growth of *Rhizoctonia*.

In yet another embodiment, the effective amount is sufficient to inhibit growth of *Sclerotinia*.

These representative embodiments are in no way limiting and, are described solely to illustrate some aspects of the invention.

DETAILED DESCRIPTION OF THE INVENTION

The present invention generally relates to formulations suitable for agricultural use comprising cinnamon oil, diallyl disulfide, at least one solvent selected from the group consisting of soybean oil, methyl oleate, ethyl lactate, and methyl soyate, and an emulsifier, wherein said formulations do not include an organic solvent, a surfactant, or a detergent.

The invention further relates to methods for protecting a plant from at least one pathogen comprising application to the locus, soil, or seeds of plants of an effective amount of the claimed formulations. The phrase "protecting a plant" means controlling the growth of one or more pathogens, which may involve killing the pathogen and/or slowing or arresting its proliferation. Representative pathogens include, but are not limited to, nematodes, *Pythium, Rhizoctonia*, and *Sclerotinia*.

In one embodiment, the invention provides a formulation suitable for agricultural use comprising cinnamon oil, diallyl disulfide, at least one solvent selected from the group consisting of soybean oil, methyl oleate, ethyl lactate, and methyl soyate, and an emulsifier, wherein said formulation does not include an organic solvent, a surfactant, or a detergent. In a preferred embodiment, the emulsifier is polyethylene sorbitol hexaoleate.

In a preferred embodiment, cinnamon oil comprises from 10 to 50% by weight of the total formulation, diallyl disulfide comprises from 3 to 15% of the formulation, soybean oil comprises from 30 to 70% by weight of the total formulation, methyl oleate comprises about 10 to 25% by weight of the total formulation, and polyethylene sorbitol hexaoleate comprises about 5 to 15% by weight of the total formulation. The weight/weight ratio of cinnamon oil to diallyl disulfide varies from about 3:1 to about 10:1.

In a more preferred embodiment, cinnamon oil comprises about 43% by weight of the total formulation, diallyl disulfide comprises about 7% of the formulation, soybean oil comprises about 30% by weight of the total formulation, methyl oleate comprises about 10% by weight of the total formulation, and polyethylene sorbitol hexaoleate comprises about 10% by weight of the total formulation.

In yet another embodiment, the invention provides a formulation suitable for agricultural use comprising cinnamon oil, diallyl disulfide, soybean oil, ethyl lactate, and polyethylene sorbitol hexaoleate, wherein said formulation does not include an organic solvent, a surfactant, or a detergent. In a preferred embodiment, the total weight % of the cinnamon oil plus the diallyl disulfide comprises about 50% by weight of the total formulation.

The methods of the present invention are carried out by applying to the plant host locus, soil, the substrate in which it is to be growing in, or seeds of plants in need of such treatment, an effective amount of the claimed formulations. The phrase "effective amount" means a sufficient amount of the formulation to provide the desired effect. The amount may vary depending on the specific plant, degree of infestation, and other factors, those skilled in the art are aware of.

A measure commonly used by those skilled in the art to determine the effectiveness of anti-pathogenic formulations is $LC_{50}$. This number represents the concentration of active ingredient at which 50% of the pathogenic organisms die.

The formulations may be applied by spraying, pouring, dipping, chemical irrigating, in the form of concentrated liquids, solutions, suspensions, and the like. They may be applied, for example, in the form of dilute solution, in a suitable natural solvent directly to the plants either as part of an irrigation schedule or as a separate application.

In one embodiment, the effective amount is sufficient to provide an acceptable level of gall reduction.

In another embodiment, the effective amount is sufficient to inhibit growth of *Pythium*.

In yet another embodiment, the effective amount is sufficient to inhibit growth of *Rhizoctonia*.

In yet another embodiment, the effective amount is sufficient to inhibit growth of *Sclerotinia*.

In one embodiment of the present invention, the formulations used in accordance with the present invention include from 1 ppm to 5000 ppm of cinnamon oil; preferably, from 1 ppm to 1000 ppm of cinnamon oil, and most preferably, from 1 ppm to 500 ppm of cinnamon oil.

As used herein, all numerical values relating to amounts, weight percentages, and the like are defined as "about" or "approximate" value, plus or minus 10%. Therefore, amounts within 10% of the claimed values are explicitly encompassed by the scope of the claims.

The following examples are offered by way of illustration only, not to limit the scope of this invention, as represented by the claims list attached herein.

EXAMPLE 1

Preparation of 50% (Combined) Cinnamon Oil Plus Diallyl Disulfide Formulation

The following amounts of the ingredients are added in the order listed, then mixed well with a magnetic stirrer until homogeneous:

43.0% by weight of the total formulation of cinnamon oil;
7% diallyl disulfide;
30.0% by weight of the total formulation of soybean oil;
10.0% by weight of methyl oleate; and
10.0% by weight of polyethylene sorbitol hexaoleate emulsifier.

EXAMPLE 2

Application of 50% (Combined) Cinnamon Oil Plus Diallyl Disulfide Formulation in Greenhouse Pot Test Tests are conducted in 2" pots containing 125 grams non-pasteurized 2:1 sand soil mix containing 2 cucumber seedlings at the 1st true leaf stage (var. Straight Eight). Each treatment consists of 4 replicate pots. Application of test materials is carried out by drenching each pot with 25 milliliters of an aqueous dispersion of the formulation being tested. Several hours after the test materials are applied, 800, second stage juveniles (J2) of freshly hatched *Meloidogyne incognita* (Root-knot nematode), are applied to each pot with the exception of the untreated control. The pots are maintained for 12-15 days at standard greenhouse temperature and lighting conditions and watered as needed for the duration of the test. At harvest, the soil is removed from the roots by rinsing the roots in water. The roots are then rated for galling on a scale from 0-9 where 0 represents no galls and 9 represents heavy galling.

Example 2. Synergistic Activity of Allyl Disulfide in a Greenhouse Pot Test

| Treatment | Average Gall Rating (0-9) |
| --- | --- |
| Untreated Control | 0 |
| M.i. (nematode) Control | 9 |
| Cinnamaldehyde at 300 ppm AI | 7.75 |
| Allyl disulfide (BAB-0294-75) at 300 ppm AI | 5 |
| Cinnamaldehyde + Allyl Disulfide 5:1 ratio at a combined total of 300 ppm AI | 2.5 |
| Cinnamaldehyde + Allyl Disulfide 10:1 ratio at a combined total of 300 ppm AI | 4 |

EXAMPLE 3

Application of 50% (Combined) Cinnamon Oil Plus Diallyl Disulfide Formulation in Greenhouse Pot Test Tests are conducted in 2" pots, as explained in Example 2 above.

Example 3. Synergistic Activity of Allyl Disulfide in a Greenhouse Pot Test

| Treatment | Gall Rating (0-9) |
| --- | --- |
| Untreated Control | 0 |
| M.i. (nematode) Control | 8.25 |
| Cinnamaldehyde at 300 ppm AI | 9 |

| Treatment | Gall Rating (0-9) |
|---|---|
| Allyl disulfide (BAB-0294-75) at 300 ppm AI | 3.25 |
| Cinnamaldehyde + Allyl Disulfide 5:1 ratio at combined total of 300 ppm AI | 1 |

The above results demonstrate the synergy between the nematicidal metabolites and diallyl disulfide according to the present invention.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the active agents and excipients of the invention, may be made without departing from the spirit and scope hereof.

The invention claimed is:

1. An agricultural formulation for suppressing plant pathogens consisting of cinnamon oil and/or cinnamaldehyde, diallyl disulfide, at least one solvent selected from the group consisting of soybean oil, methyl oleate, ethyl lactate, and methyl soyate, and an emulsifier.

2. An agricultural formulation for suppressing plant pathogens use consisting of cinnamon oil and/or cinnamaldehyde, diallyl disulfide, soybean oil, methyl oleate, and an emulsifier.

3. The formulation of claim 2, wherein said emulsifier is polyethylene sorbitol hexaoleate.

4. The formulation of claim 3, wherein the cinnamon oil comprises from 10 to 50% by weight of the total formulation, the diallyl disulfide comprises from 3 to 15% by weight of the total formulation, the soybean oil comprises from 30 to 70% by weight of the total formulation, the methyl oleate comprises about 10-25% by weight of the total formulation, and polyethylene sorbitol hexaoleate comprises about 5 to 15% by weight of the total formulation.

5. The formulation of claim 1, wherein the solvent is soybean oil.

6. A method for suppressing plant damage by plant pathogens, comprising applying an effective amount of the formulation of claim 1 to the locus, soil or seeds of one or more plants in need thereof.

7. The method of claim 6 wherein the ratio of cinnamon oil and/or Cinnamaldehyde to Diallyl Disulfide ranges between 3:1 and 10:1.

8. The method of claim 6, wherein said pathogen is a nematode.

9. The method of claim 6, wherein the plant is a cucumber.

10. The method of claim 6, wherein the plant is a melon.

11. The method of claim 6, wherein the plant is a tomato.

12. The method of claim 6, wherein said formulation is applied by spraying.

13. The method of claim 6, wherein said effective amount is sufficient to provide an economically acceptable level of gall reduction.

14. The method of claim 6, wherein said effective amount is sufficient to provide an economically acceptable level of inhibition of growth of *Pythium*.

15. The method of claim 6, wherein said effective amount is sufficient to provide an economically acceptable level of inhibition of growth of *Rhizoctonia*.

16. The method of claim 6, wherein said effective amount is sufficient to provide an economically acceptable level of inhibition of growth of *Sclerotinia*.

* * * * *